(12) United States Patent
Modell

(10) Patent No.: US 7,720,526 B1
(45) Date of Patent: May 18, 2010

(54) SELF-INTERFERING TOMOGRAPHY SYSTEM

(76) Inventor: Mark D. Modell, 1 Arcadia Rd., Natick, MA (US) 01760

( * ) Notice: Subject to any disclaimer, the term of this patent is extended or adjusted under 35 U.S.C. 154(b) by 1779 days.

(21) Appl. No.: 10/770,699

(22) Filed: Feb. 3, 2004

Related U.S. Application Data

(60) Provisional application No. 60/444,750, filed on Feb. 4, 2003.

(51) Int. Cl.
*A61B 5/05* (2006.01)
*G01J 3/45* (2006.01)
*G01B 9/02* (2006.01)
*G01B 11/02* (2006.01)

(52) U.S. Cl. ............... 600/476; 356/456; 356/477; 356/497; 356/407

(58) Field of Classification Search ............... 356/479, 356/450, 456, 477, 497; 600/407, 473, 476
See application file for complete search history.

(56) References Cited

U.S. PATENT DOCUMENTS

| | | | | |
|---|---|---|---|---|
| 4,906,092 A * | 3/1990 | O'Meara | ............... | 356/28.5 |
| 5,642,194 A * | 6/1997 | Erskine | ............... | 356/497 |
| 6,037,579 A * | 3/2000 | Chan et al. | ............... | 250/216 |
| 6,159,445 A * | 12/2000 | Klaveness et al. | ............... | 424/9.6 |
| 6,390,982 B1 * | 5/2002 | Bova et al. | ............... | 600/443 |
| 6,501,551 B1 * | 12/2002 | Tearney et al. | ............... | 356/477 |
| 6,525,862 B2 * | 2/2003 | Fisher et al. | ............... | 359/278 |
| 7,110,118 B2 * | 9/2006 | Unlu et al. | ............... | 356/450 |

* cited by examiner

*Primary Examiner*—Eric F Winakur
*Assistant Examiner*—Katherine L Fernandez

(57) ABSTRACT

Light from a tissue sample undergoes self-interference on a detector. A low coherence light source may illuminate the sample, and an interferometer receives light from the sample, divides and directs the received light along two paths, phase-delaying one and recombining the beams on a detector to form a signal. A processor coordinated with the phase delay and optionally with spatial scanning or detector array addresses, converts the signal to a tomographic image. Using self-interfering radiation from the sample, rather than interference of a reference source and a return signal, permits imaging with light naturally emitted by the sample, or with wavelength-shifted, delayed or induced light signals, allowing new diagnostic imaging modalities. The processor may create images in registry from different (for example, close but separable) wavelengths. Systems may also operate without an illumination source or may apply other stimuli to evoke emission from the sample.

11 Claims, 5 Drawing Sheets

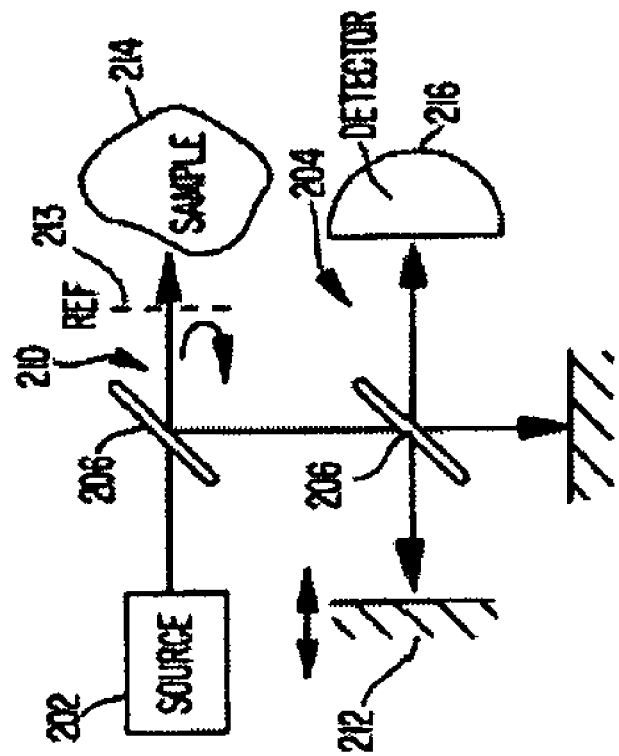
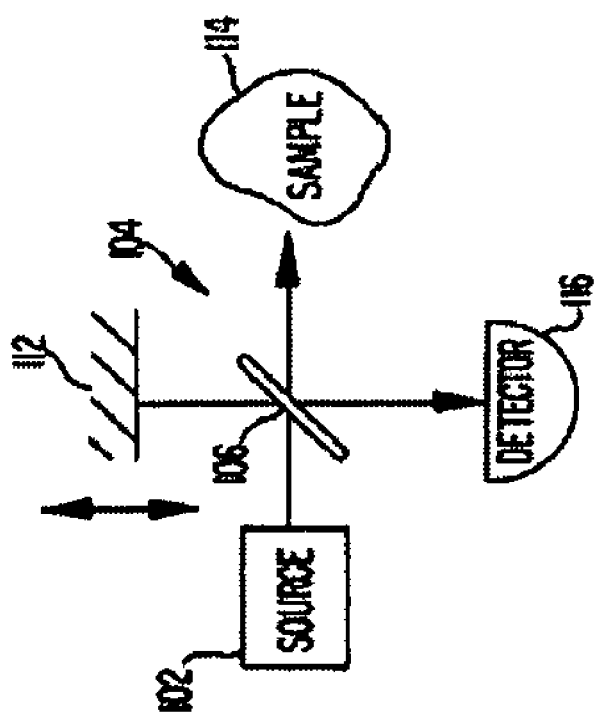
FIG. 2B
FIG. 2A

SELF-INTERFERING TOMOGRAPHY SYSTEM

This application claims priority of the U.S. Provisional Patent Application No. 60/444,750 filed on Feb. 4, 2003.

FIELD OF THE INVENTION

This invention relates generally to interferometric systems for use in optical imaging, and more specifically imaging using optical coherence tomography.

BACKGROUND OF THE INVENTION

Optical Coherence Tomography ("OCT") is a type of optical coherence-domain reflectometry that uses low coherence interferometry to perform high-resolution ranging and cross-sectional imaging. In OCT systems, a light beam from a low coherence light source is split into a reference light beam and a sample light beam. The sample light beam is directed onto a sample and the light scattered from the sample is collected and combined with the reference light beam. The combination of the sample and reference light beams results in an interference pattern corresponding to the variation in the sample reflection with the depth of the sample, along the sample beam. The sample beam typically suffers a high loss of energy due to its interaction with the sample. The reference beam serves as a local oscillator used to recover interference information at a detectable level in the return light, and typically must have a much higher energy level than the light beam returned from the sample. For example, the reference beam may have intensity under about 1% of the source, and the light returned from the sample may be substantially weaker.

In OCT, the reference beam and the collected sample beam are mixed on a photo detector, which detects the interference signal. The output of the photodetector is processed to computationally generate a cross-sectional image of the sample. The intrinsic scale of interference effects provides high-resolution (less than 10-20 micrometer) imaging of the cross-sections of the sample, making such OCT useful in biological and medical examinations and procedures, as well as in materials and manufacturing applications.

Examples of such a system have been described in U.S. Pat. No. 6,134,003 ("the '003 patent"), which particularly describes one construction based on an interferometer that includes a broadband optical radiation source; an optical radiation detector; a reference optical reflector; a first optical path leading to the reference optical reflector; and a second optical path including the sample that is to be imaged. A beam divider splits the optical radiation from the optical radiation source along the first optical path to the reference reflector and along the second optical path to the structure being viewed. The optical radiation detector is positioned to receive reflected optical radiation from the reference reflector and reflected optical radiation returning from the structure. Light from these two paths self-interferes, so the detector generates a signal in response to the reflected optical radiation. A processor utilizes the signals from the detector to generate an image of the structure being viewed. The reference optical reflector is typically a mirror coupled to a movable actuator to provide periodic movement to the reference mirror.

The prior art system of the '003 Patent is broken down into a several major subsystems as shown in FIGS. 1, 2A and 2B of that patent, which are reproduced here as FIGS. 1,2A and 2B. These are described in the '003 patent as follows " . . . the imaging system includes an optical radiation source 2, an interferometer 4, a detector 16, and an endoscopic unit 34. The interferometer 4 may be of any of the types known to one skilled in the art. For the purposes of discussion only, the embodiment will be discussed in terms of a Michelson interferometer. However, other embodiments using the other types of interferometers are contemplated. The interferometer 4 of this embodiment includes a beam divider 6, which divides the optical radiation along a first optical path defining a reference arm 8, and a second optical path defining a measuring arm 10. The optical path defining a reference arm 8 includes a reference reflector 12. The optical path defining the measuring arm 10 includes the endoscopic unit 34.

In general, the interferometer 4 operates by transmitting radiation from the optical radiation source 2 to the beam divider 6 where it is divided and transmitted along the optical paths defining the reference arm 8 and the measuring arm 10. Light reflected from the beam divider 6 travels along the reference arm 8 and is reflected back by the reference reflector 12. Light transmitted through the beam divider 6 along the measuring arm 10 travels through the endoscopic unit 34 and illuminates a structure 14 under observation. Light reflected by the structure 14 travels back through the endoscopic unit 34 along the measuring arm 10 to the beam divider 6. The radiation reflected from the reference reflector 12 and the radiation reflected from the structure 14, is then recombined by the beam divider 6 and transmitted to the detector 16. The resulting combined radiation generates an interference pattern at the detector 16, which typically generates electrical signals representative of the combined radiation and transmits these signals to signal processing and control electronics and display unit 18 where an image of the structure is obtained and analyzed.

By changing the length of the reference arm 8, longitudinal scanning is accomplished. Longitudinal scanning provides a way of changing the location at which interference in the optical radiation being reflected from the structure 14 back through the endoscopic unit 34 is detected. If the optical radiation is emitted off axis to the longitudinal axis of the endoscopic unit 34, such scanning provides a means of viewing different tissue depths. In one embodiment, the length of the reference arm 8 is changed by moving the reference reflector 12.

By rotating the optical radiation beam emitted from the endoscopic unit 34, rotational scanning may be accomplished. In rotational scanning, a circumferential path whose radius is centered at the longitudinal axis of the endoscopic unit 34 is viewed."

"Considering each component in more detail, the optical source 2 has characteristics such as wavelength, power, coherence length, and autocorrelation function which are important factors in system performance. In some applications, near infrared sources (1.0-2.0 um) tend to penetrate deeper into many biological media than visible wavelengths and are therefore preferable. The optical radiation source 2 can include in various embodiments."

And referring to FIGS. 2A and 2B of the '003 patent, that patentee reports

"There are several varieties of interferometers that may be used in the system . . . . Although bulk optical and free space implementations are shown in these figures, there exist equivalent embodiments employing optical fibers"

as, for example, shown in the U.S. Pat. No. 5,321,501, U.S. Pat. No. 5,459,570 and U.S. Pat. No. 5,465,147. "One embodiment employs a simple Michelson Interferometer 104, as shown in FIG. 2A. In another embodiment, as shown in FIG. 2B, the interferometer 204 includes a sample reference reflector 213 in the measuring arm 210. The use of this reference reflector 213 in the measuring arm 210 allows for long displacements between a beamsplitter . . . and the sample.

Although faster scanning helps eliminate motion induced artifacts, in most living biological tissues there is a limit to how fast scanning can be accomplished due to the finite signal power that can safely be delivered to the specimen or practical considerations in mechanical scanning systems. Signal processing techniques can help eliminate any residual motion induced artifacts . . . . As shown in the interferometer 204 of FIG. 2B, by placing a sample reference reflector 213 near or on the structure, a differential measurement between the sample reference reflector and structure is possible.

This measurement is less sensitive to any path length variations along the measurement arm 210. In fact the distance to the structure 14 can be made very large. In order to maintain sensitivity, the sample reference reflector 213 must reflect enough radiation to maintain shot-noise-limited operation. The sample reference reflector 213 can be located at the distal end of the endoscopic unit 34 to help overcome potential artifacts caused by the delivery optics."

OCT based systems may be implemented with fiber optics, and an optical fiber carrying the sample light beam may be incorporated into a catheter or an endoscope for insertion into an internal body cavity or organ, such as a blood vessel, the gastrointestinal tract, the gynecological tract or the bladder, to generate images cross-sections of tissue inside the cavity or organ. The sample beam is typically emitted from the distal end of the instrument, where a prism or a mirror, for example, directs the sample light beam towards a wall of the cavity. The optical fiber and the prism or mirror may be rotated by a motor to facilitate examination of the circumference of the cavity. In OCT systems, either the reference light beam or the sample light beam may be modulated to provide a relatively low frequency beating used as a carrier frequency. Mechanical motion may be used to scan the optical path, which essentially represents the sample depth. This motion also creates a Doppler frequency shift. The amplitude of the frequency of modulation is modulated by the intensity of the reflected and scattered light in the sample beam. The signal is then processed using a narrow band amplifier tuned to the frequency, to extract the intensity variation to produce an image.

The signal processing of these prior art systems consists primarily in extracting the interferometric signal corresponding to the location in the sample at which interference in the optical radiation being returned from the sample is detected. The interferometric signal is substantially proportional to the signal returned from the sample since the reference signal can be considered as a constant. Longitudinal scanning in the reference optical path, which changes path delay, corresponds to scanning the depth dimension of the region being imaged. Such scanning is typically achieved, for example, by moving the reference reflector. As the path length along the axial direction is thus varied, the signal processing electronics creates an image of the sample structure along the longitudinal axis and this is displayed by a suitable display unit (see, for example, the signal traces of FIGS. 7A, 7B and 7C in U.S. Pat. No. 5,459,570). The detector and signal processing electronics may be selected to provide high sensitivity and high dynamic range.

One limit to the sensitivity of the system is dictated by quantum mechanical effects in the detectors. The minimum resolvable reflection from the sample is proportional to the longitudinal velocity V of the reference mirror and the incident source signal power P. Thus, as scan rate increases, greater signal power is needed to maintain a given receiver-sensitivity, and the system should therefore be optimized to enhance signal detection. For example, to achieve this sensitivity, a low noise transimpedance amplifier and sufficient reference signal power may be used to ensure that the shot-noise from the reference arm power dominates the thermal noise of the transimpedance amplifier. Various signal processing approaches may enhance the recoverable information. For example, the reference light beam or the sample light beam may be modulated to provide a relatively low frequency beating used as a carrier frequency, and the processor may synchronously demodulate the signal to extract an envelope corresponding to the interference intensity as described above. The signal processing electronics can also employ phase sensitive detection techniques and inverse scattering theory or bandwidth expansion techniques to extract enhanced resolution or other signal information. One method to enable phase sensitive detection is for the electronic processing unit to consist of an anti-aliasing low pass filter followed by an A/D converter. Suitable digitizing may be effected, for example with a 12- to 16-bit device running at about twice the intermediate frequency. It has further been proposed to extract velocity data from the received signal when the imaged region contains moving scatterers, such as blood cells, by extracting Doppler frequency information from the return signals, e.g., with a spectrum analyzer. The velocity of the imaged scatterers is then detected, with a spatial resolution about equal to the coherence length. This technique is useful tool for analyzing moving blood or flowing bodily fluid (secretions), pulse rate, etc. A digital signal processing unit (DSP) unit may be used to perform such frequency analysis in several ways to simply display the derived velocities, for example by implementing a bank of bandpass filters around a nominal zero Doppler frequency signal.

The foregoing description is believed to accurately represent the state of the art in endoscopic OCT imaging and its common variations.

When compared to conventional forms of optical imaging, OCT will be seen to have several limitations. It requires splitting of a small portion of the source beam to provide a coherent reference beam, and the intensity of this portion governs several aspects of the quality achievable in the image. Moreover, since image construction depends on phase differences between light returned from the tissue and this reference beam, conventional OCT is unable to image with different, or secondary return light, such as tissue fluorescence or dye-enhanced secondary emissions. This is a limitation for many diagnostic requirements. Additionally, tissue should be in within a length of longitudinal scanning or otherwise it would require changing of this scanning to adapt the system to the various distances to the tissue being imaged. It is especially difficult to achieve when the light is brought in and out of the tissue through the fiber optic means (see for example, Iftimia N, Bouma B E, Tearney G J, "Adaptive ranging in cardiovascular OCT imaging", SPIE Proceeding Vol. 5316, *Coherence Domain Optical Methods and Optical Coherence Tomography in Biomedicine* VIII, San Jose, Calif., 2004). The difference in the index of refraction, polarization and other optical properties of the tissue and their variations during measurements relative to the reference arm requires additional complexity in order to reduce the effect of theses variations.

SUMMARY OF THE INVENTION

The present invention is implemented with an imaging system arranged to illuminate a sample that is to be imaged, such as tissue or the like, and to collect light from the sample. The imaging system may include a low coherence light source that illuminates the sample, and an interferometer that receives light re-emitted from the sample. The interferometer is arranged to pass this light to a detector. The interferometer includes a beam divider that divides the optical radiation collected from the sample into two optical paths, and further includes two optical path reflectors placed in these paths to direct the optical radiation along the paths such that the divided beam is recombined. The detector is positioned to receive the combined radiation from both paths and to generate a signal in response to the collected optical radiation from the sample structure. Thus the divided re-emitted signal undergoes self-interference, and is detected by the detector. The interferometer introduces a changing optical delay in one optical path relative to the other to provide a longitudinal scan of the sample structure being imaged. A processor processes the output from the detector to extract data corresponding the structure being imaged and at depths corresponding with the delay to generate an image of the structure being viewed. Thus, an image is reconstructed based upon the interferometric signal from a split and then recombined signal from the sample, rather than interference of a reference signal and a return signal.

One of the optical path reflectors may be coupled to a movable actuator that periodically moves the optical path reflector to provide an optical delay to scan the optical depth of the sample. Other embodiments can be configured to scan the sample depth, for example, by using by rotating a gear-like mirror, fiber stretcher, or phase shifter, an acousto-optic frequency shifter or by change in phase delay using a grating-based phase controlled delay line. All of these methods for affecting the longitudinal scan can also be used for the frequency modulation to shift the output signal from the DC region and enable using narrow band frequency amplification.

Other or further embodiments of the invention may collect radiation re-emitted from the sample that is at different wavelengths than the radiation sent to the sample. The re-emitted radiation is separated into at least two beams such that the re-emitted radiation of one wavelength is received by one optical radiation detector and return radiation of a second wavelength is received by a second radiation detector. The processor may process the outputs from both detectors to generate images of the structure of the sample for both wavelengths, separately or combined.

BRIEF DESCRIPTION OF THE DRAWINGS

These and other features of the invention will be understood from the description and claims below, taken together with the drawings of illustrative embodiments, wherein FIG. 1, 2A and 2B illustrate prior art OCT devices;

DETAILED DESCRIPTION

Figure 1:
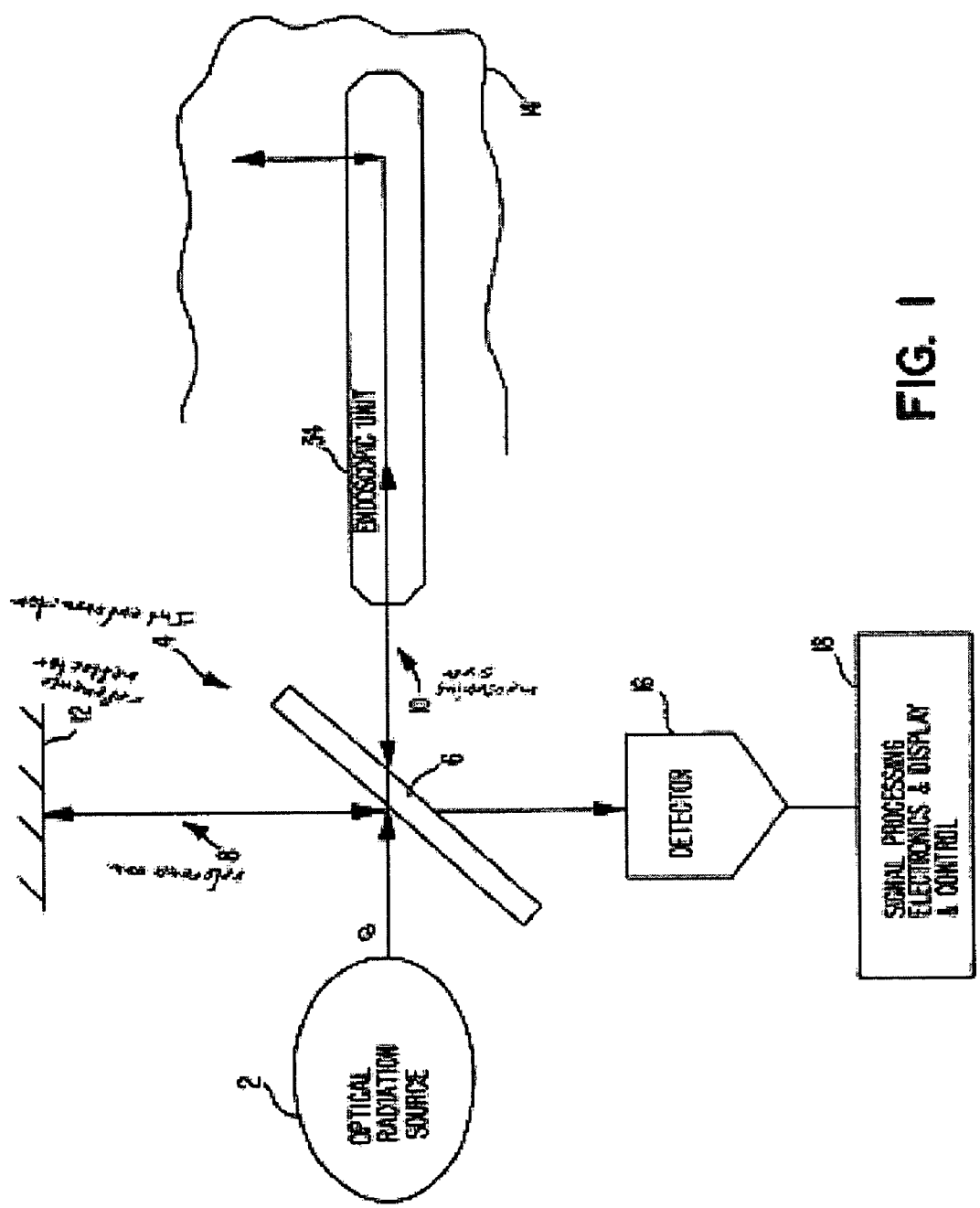
Figure 3A:
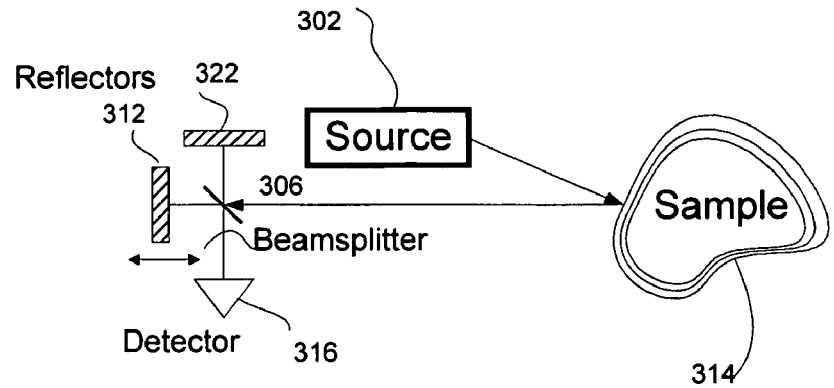
FIG. 3A schematically illustrates a first embodiment of the invention.

The optical system of one embodiment of the invention is schematically presented in FIG. 3A. A low coherence light source 302 emits optical radiation with a short coherence length and this is directed, either directly or via a fiber or other light guide, to illuminate a sample 314, such as tissue or an object that is to be imaged. Radiation re-emitted and collected from the sample 314 is divided by a beam splitter 306 into two signals, directed along two optical paths. Each of these radiation beams propagates to a corresponding optical path reflector, 312 or 322, respectively, which reflects the radiation back to the divider 306 and to a detector 316 that is positioned to receive the radiation. The output signal of the detector represents the structure of the sample and is processed to develop an image. One of the optical path reflectors can be moving so that it creates a variable optical delay; this has the effect, in subsequent signal processing, of scanning the sample depth. For some applications one may select an illumination source with a coherence length to provide a depth resolution of 10 to 20 microns or less. For other application longer coherence length or lower resolution will be useful.

Figure 3B:
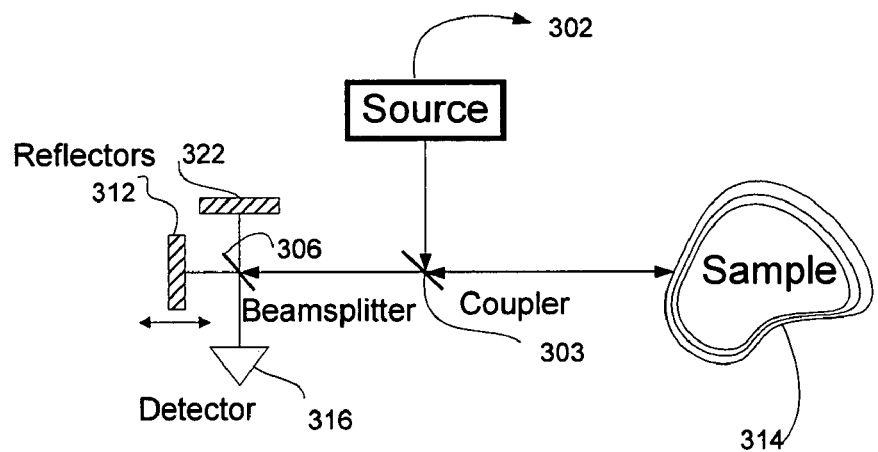
FIG. 3B schematically illustrates a second embodiment of the invention.

FIG. 3B illustrates another embodiment of the general scheme of the invention. Here the radiation from source 302 propagates, directed by a coupler 303, such as a light fiber, light pipe, articulated arrangement of mirrors or other light coupling assembly, to the sample 314. The coupler 303 also collects light from the sample and directs the collected radiation to the beam splitter 306.

Figure 3C:
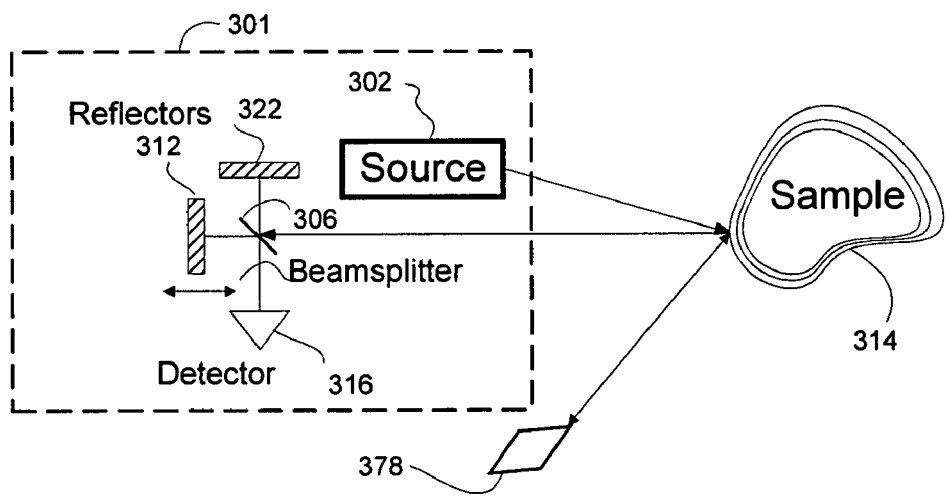
FIG. 3C schematically illustrate a third embodiment of the invention.

FIG. 3C illustrates another aspect of the invention. Here a system 301, such as one of the embodiments shown in FIG. 3A and FIG. 3B, directs light to the sample 314 and collects light from the sample 314. Additionally, a position device such as a rangefinder, 378 determines the relative position, e.g., distance from the system to the sample. This distance can be determined from the surface of the sample, or particularly advantageously from the depth of the sample. The set or detected relative position or distance is used to enhance the localization accuracy of the area probed by the system. This aspect of the invention is particularly advantageous when the sample is part of the larger object such as a lumen of a blood vessel, or other lumen or organ of a human or animal body, and/or when the system is imaging the volume of the sample using non-elastic re-emission from the imaged volume. The rangefinder or relative positioning device 378 can be implemented by utilizing various devices such as ultrasound and light or other electromagnetic wave based with the direct time-of-flight or triangulation, or multi angle or positioning devices, MRI or CT, or other imaging devices, or a combination of a physical structure with a ranging and algorithm-based detection device.

In yet another embodiment, the incident light is directed to the sample and/or the emitted or re-emitted light is collected light from the sample at two or more different angles or locations. Utilizing images derived from radiation received from multiple directions, the localization of the imaged volume is determined. This embodiment may be implemented by utilizing two or more systems simultaneously, or by using a single system to probe along at two directions at different times. Both methods of operation may also be combined in the same instrument.

Figure 4:
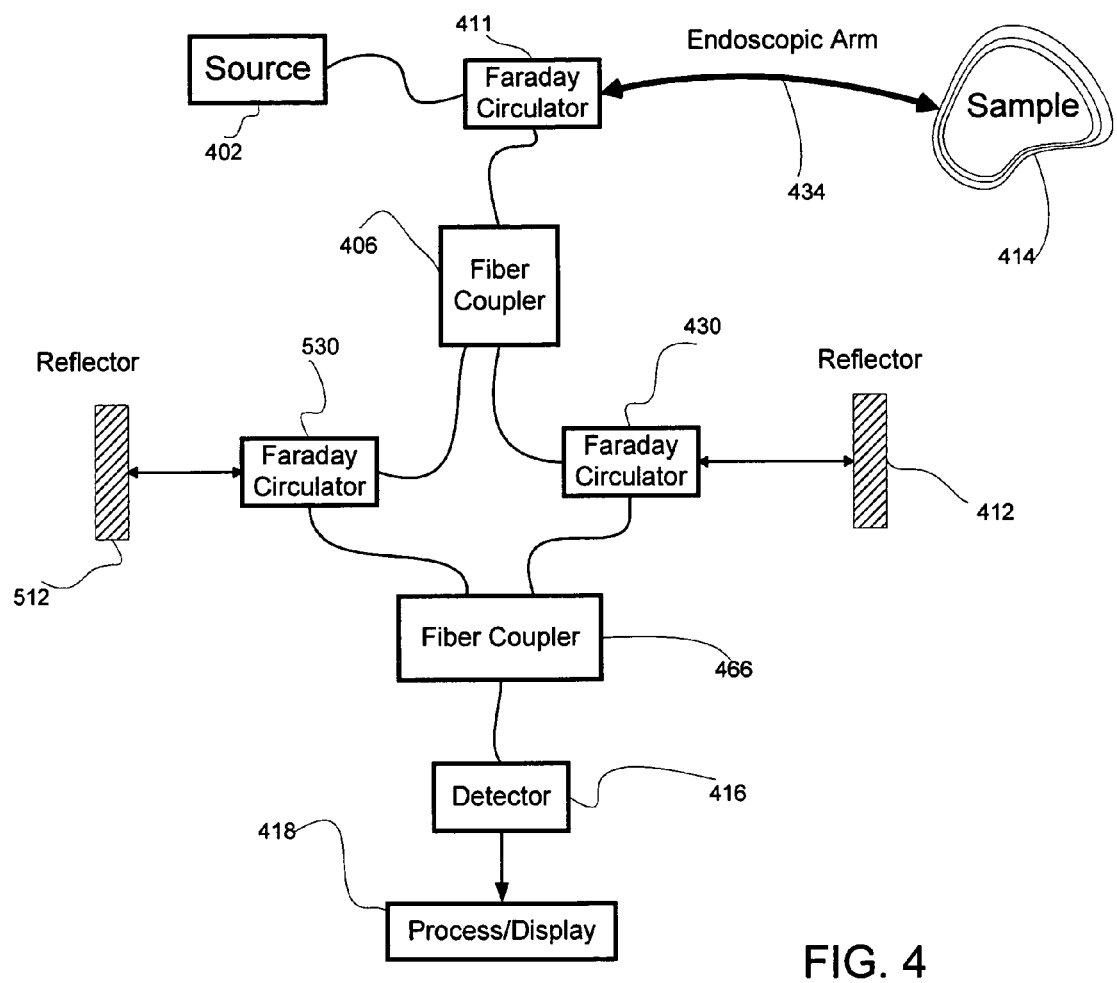
FIG. 4 shows another embodiment of the invention.

An interferometer assembly, represented by the beam splitter 306 and the optical path reflectors 312 and 322, can be implemented in a fiber-based embodiment to achieve higher efficiency. One such fiber-based embodiment is shown in FIG. 4. In this embodiment, short coherence length radiation from a source 402 is coupled into an optical fiber, which guides the radiation to a Faraday circulator 411. The Faraday circulator has an output port connected to pass the radiation into the arm of an endoscope. The radiation guided by the endoscopic arm hits the sample 414. The radiation returned from the sample is collected by the distal end of the endoscopic arm and is guided back to the circulator 411, which directs the light via its third port into a fiber coupler 406. In this assembly, the Faraday circulator maintains the light collected for the sample separate from the source illumination beam, so that the fiber coupler 406 receives just the collected light. The fiber coupler 406 divides the radiation it receives into two parts and directs them, e.g., via corresponding Faraday circulators 430, 530, to optical path reflectors 412 and 422, correspondingly. The optical path reflectors 412 and 422 reflect the radiation, and the reflected radiation is directed via the remaining port of the circulators 430, 530 respectively, guided by the corresponding fibers into a fiber coupler 466, such as a Y-junction coupler that has a single fiber output, thus combining the two beams. The combined radiation of the single fiber output is guided into the detector 416, which produces an electrical output signal response. The signal response produced by the detector is sent to a computer 418, where it is processed to display the structure of the sample 414. As in other embodiments, one of the optical path reflectors 412, 512 is moved to provide a variable optical delay and implement a depth scan of the sample. In one implementation the system employs a single mode fiber or single mode polarization preserving fiber. In other embodiments of the system one can utilize multimode fibers and even bundle of fibers.

In any of these embodiments X and/or Y scanning may be carried out to detect depth information over a two-dimensional region or area of the sample. Such area or linear scanning mechanism may be of known type and requires no further discussion.

The interferometer signal from the detector represents the autocorrelation of the collected radiation originating from the sample at a depth corresponding to the optical delay introduced by the longitudinal scanning of the one or both of the optical path reflectors. The computer performs suitable signal processing to transform the time-varying interferometric signal output of the detector into an image signal representing the re-emitted radiation from the sample depths corresponding to the optical delay scanning. The processor may, for example process the interferometric signal by applying a general convolution. It can be described in the simplified manner as follows. The signal for each delay is the value of the integral over the longitudinal axis coordinate of the product of the three terms: coherence function of the source, the re-emitted wave from the sample, and the same re-emitted wave offset by the optical delay. In the first approximation the coherence function can be considered as a delta function since the light has a short coherence length. Thus, in the first approximation, the interferometric signal is the integral of the product of the re-emitted wave multiplied on itself offset by the optical delay. Changing the delay and measuring the interferometric signal make the interferometic signal a function of the delay, i.e. the integral becomes the convolution of re-emitted wave over the delay. Applying the convolution theorem, the re-emitted signal as a function of depth (the longitudinal axis coordinate) is extracted from the above integral. This may be done, for example, by applying a Fourier transform to the convolution integral, then taking a square root of this transform and then applying a reciprocal Fourier transform of the latter, getting the amplitude of the re-emitted wave as a function of the sample depth along the longitudinal axis. The value of the intensity of the re-emitted light as a function of depth will be the square of this amplitude.

After that the processing electronics creates an image of sample structure along the longitudinal axis. One additional advantage of this method is that the correlation function will also measure degree of disorganization of the sample. By utilizing this function we can extract not only the distribution of scattering (i.e. the distribution of the refractive indexes) (which could also be provided by the prior art), but also the structure (i.e. the organization or disorganization) of the tissue in any particular location.

In some embodiments, the radiation can also be modulated in one optical path to form a carrier frequency, so that demodulation detection techniques can be applied to improve detection of the return signal. Modulation as well as a variable optical delay can be implemented in either one of the optical paths or in both, and this may be done with the same frequency and speed for both paths, or different. The processor demodulates the signals accordingly.

In another embodiment, instead using low speed analog-to-digital conversion (ADC)—which operates on the envelope of the interference signal a system uses high speed ADC to digitize the interference signal and record the interference signal variation inside the envelope (see Morgen U., Drexler W., Kartner F X, et al, "Spectroscopic optical coherence tomography", *Optics Letters,* 2000, Vol 25, No. 2, pp. 111-113). This high speed ADC preserves a spectral information in the signal. A processor utilizes the Fuorier transform of the signal to extracts the spectral characteristics of the light-tissue interaction localized along the scanning depth. These localized spectral characteristics are useful, since they correspond in known ways to many tissue characteristics such as color, absorption, existence and size of scatterers such as cells or nuclei, their densities and other histopathological or tissue indicators.

In another embodiment, instead of scanning the depth by moving the mirror and directing the light to a single detector, one can utilize a fixed mirror and direct light through spectrograph onto a CCD. The depth information is extracted from the interferogram on this CCD by Fourier transformation processing similar to the processing scheme (Hausler G and Linder M W, ""Coherence Radar" and "Spectral Radar"—New Tools for Dermatological Diagnosis", *Journal of Biomedical Optics,* 3(1), 21-31 (1998), Wojtokowski M, Leitgeb R, Kowalczyk A, et al, "In vivo human retinal imaging by Fourier domain optica coherence tomography", *Journal of Biomedical Optics,* 7(30), 457-463 (2002)). In this approach, the broader spectral band source is used. Rather then a broader spectral band source, this embodiment can employ the light source tunable over a broad spectral band and use a single detector. As in the previous embodiment, these localized spectral characteristics are useful, since they correspond in known ways to many tissue characteristics such as color, absorption, existence and size of scatterers such as cells or nuclei, their densities and other histopathological or tissue indicators.

In another embodiment, the source can emit radiation containing at least two wavelengths selected close enough together so that the radiation corresponding to them in the sample interacts with the sample or tissue in the same manner. The wavelengths are also sufficiently close that when mixed together, they produce a heterodyning signal with a frequency corresponding to the difference of the optical frequencies of the original wavelengths that is low enough to be detected by the detector and passed further in the channel. At the same time these wavelengths have to be sufficiently apart from each other so that they can be separated (resolved) by the beam splitter. It is possible to separate two radiations with the wavelengths as close as 0.03 nm (see, for example, Jean-Pierre Laude, "History and technology of wavelength division multiplexing", *OE Reports*, October 1997, Jeff Hecht, Speeding up transmission rates with slower signals", *LFW*, November 2002. This wavelength difference corresponds to 5 GHz difference of the optical frequencies and, thus, produces the 5 GHz heterodyne signal that can be detected by the photodetector (see, for example, SIR5-FC detector from Thorlab, Newton N.J. or RP192 APD receiver from Multiplex, Plainfield, N.J.). This arrangement allows one to separate the collected light by wavelength to direct it along the two paths.

Different forms of imaging may be carried out, i.e. various physical interactions of the illuminating light with the sample or tissue or physical responses of the tissue or sample to the illuminating radiation can be utilized. The radiation collected from the sample can be at the same wavelength as the initial radiation from source, in case of the scattered back and/or reflected radiation. Alternatively, the collected radiation can be at a wavelength different from the wavelength of the original (source) radiation. Such collected radiation could be any non-elastic re-emission by the sample, for example, fluorescence emission (from one or several natural chromophores in the sample or tissue or from injected fluorescing agents), or could be Raman or Raleigh emissions. Thus, the present invention, relying on self-interference of the return beam to effect tomographic imaging, may operate with re-emitted light quite different from the source light. This allows the collected light to be simply separated from the much large source light. It may also be identified (e.g. by correlation with a library of known signals) with a diagnostic state or local condition such as presence of a metabolite or toxin, a local Ph, or other conditions of interest. These are improvements over the prior art imaging wherein the reference beam is taken from the source, either directly or through a reference mirror or component.

Figure 5A:
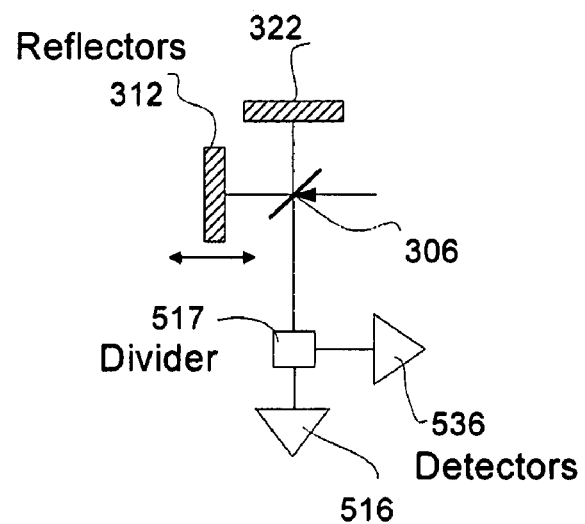
FIG. 5A illustrates a multi-wavelength imaging embodiment.
Figure 5B:
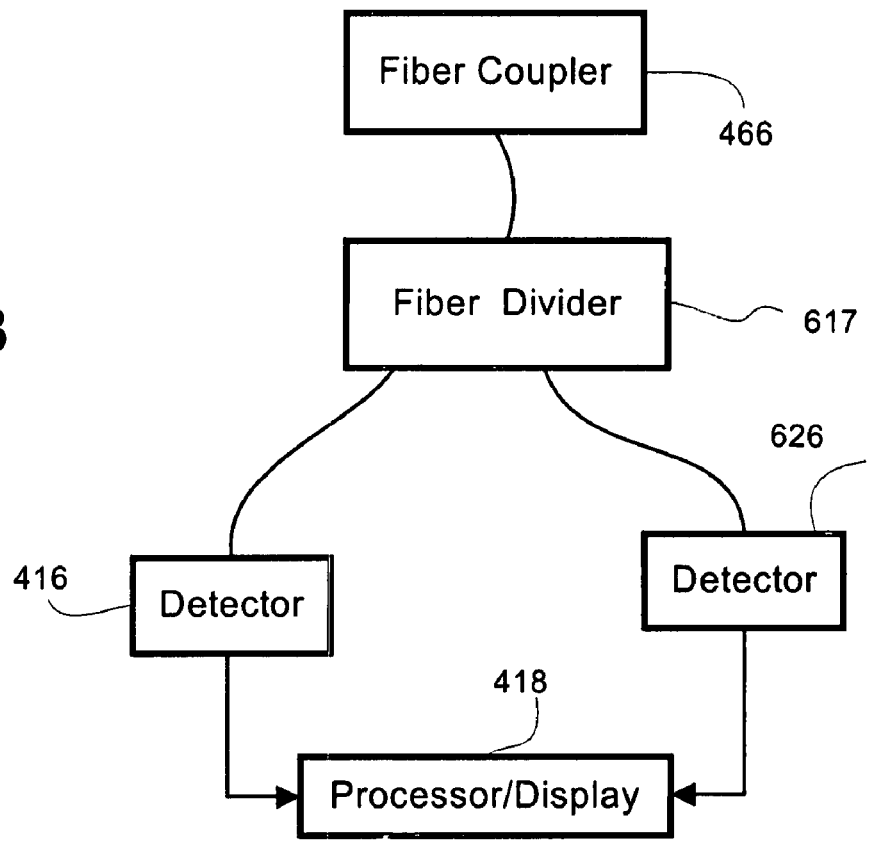
FIG. 5B illustrates another multi-wavelength imaging embodiment.

The image produced by the processor from the detector signal corresponds to these re-emissions. Various refinements may also be carried out using only the collected light. In order to be able to separate the elastic from non-elastic returned responses, and/or to see at least two responses at the same time, a dichroic or other wavelength divider 517 may be introduced into the optical system after the beam splitter 306 (see FIG. 5A), so that the each response is guided to a corresponding one of two detectors, 516 and 536. Similarly, for a fiber-based system, a fiber dichroic or other wavelength divider 617 may be placed after the fiber or other light coupler 466 (see FIGS. 4, 5B) so that each response gets to its own detector 416 and 626, respectively. A narrow band filter may also be placed before each detector to accommodate a complicated nature of the returned signal and remove unnecessary or interfering wavelengths that would otherwise contribute to, and possibly overwhelm, the detector output signal. When using two detectors in this fashion, each detector output may be processed to provide an image corresponding to its signal, and the two images, such as an optical image and a dye uptake image, are in registration with each other.

By impregnating the sample with one or more agents, the returned signal may be enhanced, and tomographic images corresponding to the specific agent are formed by the processor. These agents can be selected to enhance one or more endogenous properties of the sample or its surface, for example, to absorb, and/or to scatter, and/or to reflect, and/or to fluoresce, and/or to produce or enhance Raman signal. For example, an index matching fluid may be used to eliminate surface reflection or scattering and enhance the subsurface returned signal, or an index mis-matched fluid may be used to increase the returned scattering signal, or to create a specular reflection from the sample surface, or to enhance the emitted light from the boundary of the volume containing the emitting matter. Alternatively, an agent may added which is itself an absorber, scatterer, reflector, fluorescence emitter, Raman or Raleigh scatterer, or other inelastic signal emitter. These agents can be specific or non-specific to certain features or properties of the sample. For example, the agent may be adapted to accumulate at or attach to a blood vessel, or lipids, calcifications, cell nucleic matter, DNA sites, neoplastic or tumorous tissue, etc. A suitable agent may also be used simply to shift wavelengths and allow collected signals to be more readily separated from scattered source radiation for more effective detection and processing, contrast enhancement or the like. These agents can be created, for example, using nanotechnology tools, including nanotubes, quantum dots, nanoshells and dendrimers with specific or nonspecific targeting of tissue, or cellular, or subcellular, or molecular structure, c (see, e.g. A. J. Haes and R. P. Van Duyne, "A Highly Sensitive and Selective Surface-Enhanced Nanobiosensor", *Mat. Res. Soc. Symp. Proc.* Vol. 723 (2002)).

In all of the above cases, a source with multiple wavelengths may be used to achieve the heterodyning effect with several close wavelengths as described above.

In yet another embodiment, the imaging system need not include an illuminating source at all. In this case, luminescence radiation is emitted from the sample either without any external stimuli (natural luminescence), for example, such as bioluminescence or chemiluminescence or with some chemical or thermal stimulus, or electromagnetic (other then light) or acoustic stimulus, or some combination of them. Diagnostic utility is greatly enhanced because different form radiation may be best suited for indicating specific conditions in the body, tissue or other samples or assays. (see, for example, M. Nakano, "Detection of Active Oxygen Species in Biological Systems', *Cellular and Molecular Neurobiology*, Vol. 18, No. 6, 1998; ed. F. A. Popp, "Biophoton emission", *Experientia*, Vol 44/#7, pp. 543-630, 1988; K. Faulkner, I. Fridovich, "Luminol and Luciferin as Detectors for $O_2^{\cdot-}$", *Free Radical Biology & Medicine*, Vol. 53 pp. 447-451, 1993.) One or more of the modulation means discussed for other embodiments can be employed here as well. Preferably, in order to determine the surface of the sample as zero point of the depth measurements (i.e. the zero of the longitudinal axis), some form of radiation (not necessarily optical) can be employed. e.g., for echo or reflection ranging. Thus, embodiments of the invention permit enhanced diagnostic imaging by interference tomography of endogenous, or exogenous or conditioned light signals from the subject, and permit the source light to be entirely diverted or suppressed from the image, or not to have any light source at all, while still achieving an interferometric image of the subject along its depth.

In various embodiments, with or without the illuminating source, the emitted or re-emitted light from the sample can be modulated and/or enhanced and/or otherwise affected in a desired way by the external stimuli such as X-ray, light, ultrasound, microwave, etc, energy. Such improvement can be achieved with the endogenous or exogenous chemicals in the sample with or without the enhancement agent in the sample. For example, X-ray energy incident on the sample can be used to excite an endogenous agent, or ultrasound radiation can be applied to the sample to modulate light emitted from molecules in the sample (native or endogenous).

Instrument of the invention can employ an array of channels similar or identical to simultaneously probe plurality of points in the sample to be imaged and various pipelined processing arrangement can be employed for image gathering or construction.

This invention can be employed for imaging of various tissues of body organs in vivo as well as in vitro, for example, such as skin, cervix, colon, stomach, bladder, esophagus, brain, etc. It can be used as a stand-alone device or incorporated in the endoscopic, colposcopic or other tools used by the physicians, veterinarians and or medical technicians for 2-dimensional or 3-dimensional imaging.

The invention is not limited to imaging of biological tissue but can be applied to objects of all kinds having suitable optical properties. Thus it can be used for tomographic examination of paintings or artwork, of living or preserved plants, mineral structure and in the great variety of objects.

I claim:

1. An optical system comprising:
   an assembly arranged to collect short coherence length light from a sample, a detector;
   an interferometer arranged to receive the light collected from said sample and divide said collected light into at least two optical paths and pass the collected light to said detector, said interferometer comprising an adjustable optical delay device for introducing a delay which causes interference in the collected light, operative on at least a portion of the light collected from the sample;
   wherein said detector forms a self-interference signal from light collected from the sample, representative of structure of said sample over a depth and corresponding to said delay and further including a processor operative to form a tomographic image of the sample in response to detected signals at corresponding delay.

2. The optical system of claim 1 wherein said assembly includes a probe selected from the group consisting of a non-endoscopic probe and an endoscopic probe.

3. The optical system of claim 1 wherein said light collected from said sample includes light emitted by the sample, the light emitted by the sample including a form of light selected from the group consisting of bioluminescence, chemiluminescence, other luminescence without any external stimuli, and luminescence formed with some chemical, thermal, electromagnetic (other then light), acoustic or other stimulus, and combinations thereof.

4. The optical system of claim 1, further including an illuminating assembly comprising a short coherent length light source and means for directing the light source at the sample, wherein the means for directing includes one or more assemblies selected from the group consisting of: a probe, an endoscopic probe and an optical scanning system for directing light from the source to a desired region of the sample.

5. The optical system of the claim 4, wherein said light collected from said sample is elastic or non-elastic re-emission by the sample and the re-emission includes light of one or more types selected from the group consisting of: reflection, scattering, fluorescence, Raman scattering and Raleigh scattering light.

6. The optical system of claim 4 wherein said detector spatially separates broad band light re-emitted by said sample and photodetects said spatially separated light, wherein said detector comprises an optically dispersive element and an optical detector, and said processor produces images of said structure in situ in response to spectral signals from said detector.

7. An optical imaging method comprising the steps of:
   i) collecting light originating in a sample
   ii) passing the collected light through an interferometer assembly arranged for dividing and recombining the collected light as self-interfering light
   iii) detecting the recombined light to produce a signal from passing the recombined light to a detector to produce a signal and
   iv) processing said signal to form an image of the sample over depth.

8. The optical imaging method of claim 7, wherein the interferometer is arranged to pass light to at least two detectors and said detectors each detecting light at a different wavelength whereby collected light forms at least two images of said sample; at least one image for each of said wavelengths.

9. The optical imaging method of claim 8 wherein said processing forms said images in registry.

10. The optical imaging method of claim 7 wherein the step of collecting includes collecting light that include two wavelengths optically separable by wavelength and sufficiently close to each other so that when combined on the detector they form an electrical beat signal within bandwidth of the processing to yield interference/depth information for the image.

11. An optical system comprising
   an assembly arranged to collect short coherence length light from a sample,
   a detector;
   an interferometer arranged to receive the light collected from said sample and divide said collected light into at least two optical paths and pass the collected light to said detector, said interferometer comprising an adjustable optical delay device for introducing a delay which causes interference in the collected light, operative on at least a portion of the light collected from the sample;
   wherein said detector forms a self-interference signal from light collected from the sample, representative of structure of said sample over a depth and corresponding to said delay
   wherein the assembly collects light from a line or region of the sample and the system produces a depth image of that line or region.

* * * * *